(12) United States Patent
Klesius et al.

(10) Patent No.: US 7,988,977 B2
(45) Date of Patent: Aug. 2, 2011

(54) **MODIFIED LIVE *AEROMONAS HYDROPHILA* VACCINE FOR AQUATIC ANIMALS**

(75) Inventors: Phillip H. Klesius, Auburn, AL (US); Craig A. Shoemaker, Notasulga, AL (US); Joyce L. Evans, Chestertown, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/380,520

(22) Filed: Feb. 27, 2009

(65) Prior Publication Data

US 2010/0221286 A1     Sep. 2, 2010

(51) Int. Cl.
*A01K 63/00*     (2006.01)
*A61K 48/00*     (2006.01)
*A61K 49/00*     (2006.01)
*A61K 39/02*     (2006.01)

(52) U.S. Cl. .............. 424/200.1; 424/234.1; 424/235.1; 424/93.2; 424/9.2

(58) Field of Classification Search ................. None
See application file for complete search history.

(56) References Cited

U.S. PATENT DOCUMENTS 6,248,329 B1 *   6/2001   Chandrashekar et al.   . 424/191.1

OTHER PUBLICATIONS

Ellis (Chapter 29 of Vaccines, Plotkin, et al. (eds) WB Saunders, Philadelphia, 1998, especially p. 571, paragraph 2).*

* cited by examiner

*Primary Examiner* — Robert A Zeman
*Assistant Examiner* — Nina A Archie
(74) *Attorney, Agent, or Firm* — John D. Fado; Evelyn M. Rabin

(57) ABSTRACT

Safe and effective live vaccines against *Aeromonas hydrophila* of fish were created through the induction of rifampicin resistance in native *Aeromonas hydrophila* isolates; these including rifampicin-resistant mutants NRRL-B-50040 and NRRL-B-50041. Single immersion exposure of fish stimulated acquired immunity against virulent *Aeromonas hydrophila* infection.

16 Claims, 1 Drawing Sheet
(1 of 1 Drawing Sheet(s) Filed in Color)

MODIFIED LIVE *AEROMONAS HYDROPHILA* VACCINE FOR AQUATIC ANIMALS

BACKGROUND OF THE INVENTION

1. Field of the Invention

This invention relates to a novel vaccine against motile *Aeromonas* septicemia which does in fact provide superior protection over commercial treatment involving feeding medicated feeds.

2. Description of the Relevant Art

*Aeromonas hydrophila*, a free-living, Gram-negative bacterium, is one of the most common bacteria in freshwater habitats worldwide. *A. hydrophila* infection results in hemorrhagic septicemia and heavy mortalities in cultured and wild fish. Antibiotics and chemotherapeutic drugs have been used for disease management in feed additives and in direct administration into fish pond water; however, there has been an increase in drug resistant strains (Son et al. 1997. *Letters in Appl. Microbiol.* 24: 479-482; (Harikrishnan and Balasundaram. 2005. Reviews in *Fisheries Science* 13: 281-320). Extensive research efforts and strategies have not yet resulted in the development of a safe and effective vaccine. There is still no product that has been licensed for use against the motile aeromonads within the United States (Cipriano, R. C. 2001. *Revision of Fish Disease Leaflet* 68, U.S. Dept. Interior, Fish and Wildlife Service Div. of Fishery Res., Washington, D.C.). Thus, there is a need, particularly in the aquaculture industry, for an efficacious and safe vaccine.

SUMMARY OF THE INVENTION

We have now discovered two novel rifampicin-resistant strains of *Aeromonas hydrophila* which are safe and effective live vaccines for the control of *A. hydrophila* infections in a variety of fish species. The strains of the invention were created by multiple passages of the strains of *A. hydrophila* on increasing concentrations of rifampicin-supplemented media. The resultant rifampicin-resistant vaccine mutants, which have been designated K134B mutant (NRRL-B-50040) and C1B mutant (NRRL-B-50041), are effective in providing long lasting acquired immunity against *A. hydrophila* in Nile tilapia (*Oreochromis niloticus*), channel catfish (*Ictalruis punctatus*), and other fish.

In accordance with this discovery, it is an object of this invention to provide a novel, effective vaccine against *Aeromonas hydrophila* for fish.

Another object of this invention is to provide an effective vaccine against *A. hydrophila* which may be administered by injection or bath immersion.

An additional object of this invention is to provide an attenuated *A. hydrophila* vaccine that is safe and provides long lasting acquired immunity to motile *Aeromonas* septicemia disease in fish, including Nile tilapia and channel catfish.

A further object of this invention is to improve the viability and productivity of tilapia and channel catfish aquaculture, and to reduce economic losses in the fish industry caused by motile *Aeromonas* septicemia.

Other objects and advantages of the invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

Figure 1:
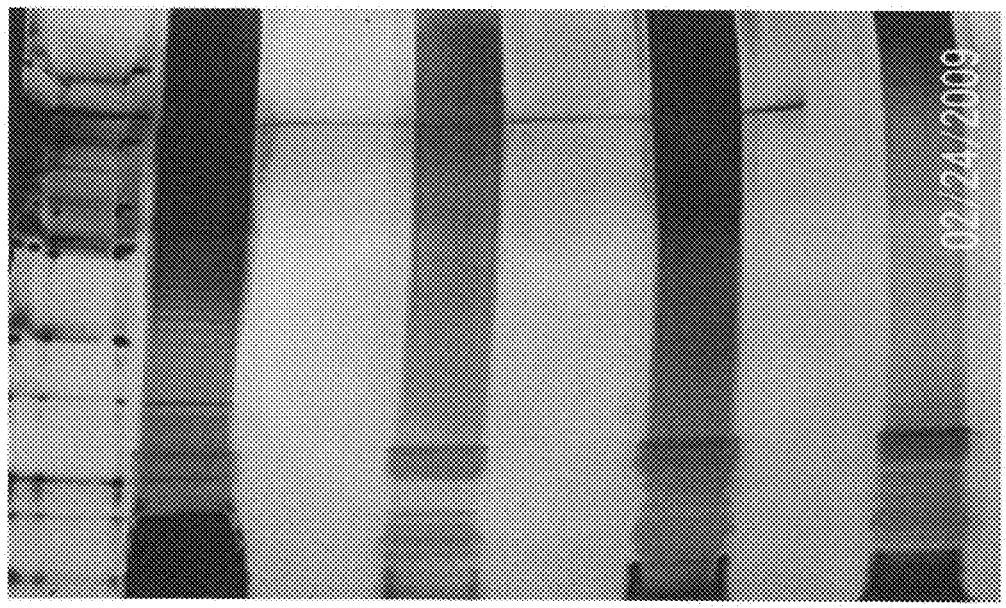
FIG. 1 depicts a comparison of *A. hydrophila* LPS profiles from C1B (Lane 2) and K134B (Lane 4) virulent parent strains and the rifampicin-resistant C1B (Lane 3) and K134B (Lane 5) avirulent mutants and molecular weight standards: Lane 1. The molecular weights (kDa) from bottom to top are 10, 15, 20, 25, 30, 40, 60, 60, 80 and 100.

The present invention provides a novel, highly protective, live vaccine against *Aeromonas hydrophila* in fish. The vaccines are effective for controlling infection of fish by any strain of *A. hydrophila*, including strains which are different from those used in the preparation of the vaccine. Moreover, this vaccine is superior to experimental killed *A. hydrophila* vaccines because it produces both antibody and cellular immunities, can be administered by more cost-effective bath immersion as well as by injection, and can provide years of protection, instead of only months.

The vaccines of the invention are also effective in controlling infection by *A. hydrophila* in a variety of fish when administered thereto. Without being limited thereto, the vaccine is especially beneficial for the treatment of tilapia (*Oreochromis* sp.), channel catfish (*I. punctutus*), American, European, and Japanese eels (*Anguilla* sp.), salmonids (*Oncorhynchus* sp. and *Salmo* sp.), striped bass and hybrid-striped bass (*Morone chrysops* X *M. saxatilis*), flounders (*Seriola* sp.), seabream (*Sparus* sp.), sea perch (*Lates calcarifer*), and the estuarine grouper (*Epinephelus tawine*), walleye (*Zander vitreum*), centrachids (such as large-mouth bass, *Micropterus salmoides*), brown bullheads (*Nebulosus* sp.) bait minnows (*Pimephales promelas*), golden shiners (*Netemigonus crysoleucas*), goldfish (*Carassius auratus*), carp (*Cyprinus carpio*) and aquarium fish species such as black mollies (*Poecilia sphenops*) and platies (*Xiphophorus maculates*). The use of this modified live *A. hydrophila* vaccine offers several benefits that include reducing disease loss in fresh and marine water fish and eel production, diminishing the food safety risks to humans, and reducing the contamination of water by *A. hydrophila* that may be discharged in the environment from fish production systems.

"Vaccine" is defined herein in its broad sense to refer to any type of biological agent in an administrable form capable of stimulating a protective immune response in an animal inoculated with the vaccine. For purposes of this invention, the vaccine may comprise one or more live attenuated mutants of *A. hydrophila* having the characteristic of rifampicin-resistance.

Rifampicin-resistant strains of *A. hydrophila* of this invention were created by the multiple passaging of isolates of *A. hydrophila*. As described in detail in Example 1, serial passage of these isolates over increasing concentrations of rifampicin produces strains with an attenuated pathogenicity efficacious for the preparation of live vaccines. The attenuation achieved by high-level serial passage in culture on increasing concentrations of rifampicin virtually eliminates the pathogenicity of the bacterium toward fish. The native strain of *A. hydrophila* should be passaged a sufficient number of times such that in its new attenuated form it no longer possesses the ability of causing the disease state known as motile *Aeromonas* septicemia in tilapia, channel catfish, or other fish. The methodology for attenuation by serial passage is well known and documented in the art as exemplified by Schurig et al. (1991. *Vet Micro.* 28: 171-188), hereby incorporated by reference, who created vaccines based on modified live rifampicin-resistant *Brucella* species.

Vaccination, while being accomplishable by injection or through oral ingestion, is most efficiently done by means of aqueous immersion. The bacterial agent is prepared for administration by formulation in an effective immunization dosage with an acceptable carrier or diluent, such as water. The expressions "effective immunization dosage" and "immunologically effective amount or dosage" are defined herein as being that amount which will induce complete or partial immunity (elicit a protective immune response) in a treated fish against subsequent challenge by a virulent strain of *A. hydrophila*. Immunity is considered as having been induced in a population of fish when the level of protection for the population (evidenced by a decrease in the number of infected fish or a decrease in the severity of infection) is significantly higher than that of an unvaccinated control group (measured at a confidence level of at least 80%, preferably measured at a confidence level of 95%). The appropriate effective dosage can be readily determined by the practitioner skilled in the art by routine experimentation. One measure of protection following experimental challenge is relative percent survival (RPS) as described by Amend (1981. *Dev. Bio. Stand.* 49: 447-454) herein incorporated by reference. RPS is calculated according to the following formula:

$$RPS = 1 - \frac{\% \text{ vaccinate mortality}}{\% \text{ control mortality}} \times 100$$

A positive vaccine effect is indicated by a RPS equal to or greater than 60%. Typically, the vaccine is administered to 7-10 day old fish by bath immersion, injection, and/or any oral delivery or immersion device. Fish are vaccinated by immersion in water containing about $5 \times 10^5$ to about $1 \times 10^8$ CFU/mL of attenuated *A. hydrophila* for 10 min at a density of about 50 fish/L and a temperature of about 30° C. CFU denotes colony forming units of *A. hydrophila*. These parameters may be varied as desired such that a sufficient level of vaccination is acquired without induction of stressful conditions or loss of fish. Useable concentrations of *A. hydrophila* are considered to range from about $5 \times 10^5$ to about $1 \times 10^8$ CFU/ml of immersion medium. Useable vaccination times are seen to range from about 1 min to about 60 min, preferably from about 2 min to about 15 min. Temperature of the inoculation media may range within the physiologically acceptable limits of the fish involved, for tilapia and channel catfish preferably from about 18° C. to about 32° C., most preferably from about 20° C. to about 30° C. Concentrations of fish treated in the inoculation medium typically range from about 50 to about 100 fish/L, but, in the alternative, may be determined on a weight basis and range from about 0.5 to about 2.5 kg/L. Fish may also be vaccinated with $1 \times 10^6$ CFU/fish of *A. hydrophila* mutants by intraperitoneal (IP) injection. The vaccine can be effectively administered any time after the fish attains immunocompetence, which for tilapia is at about two to fourteen days post-hatch and for channel catfish, after 7-10 days post-hatch. Other species of fish susceptible to *A. hydrophila* can be immunized after 21-30 days post-hatch or when they become immunocompetent to modified live vaccine administered by immersion.

To produce large amounts of the rifampicin-resistant mutant *A. hydrophila* strains C1B and K134B for preparation of the vaccine, the bacterium may be cultivated under any conventional conditions and on media which promote growth of *A. hydrophila*. Without being limited thereto, the strain may be grown on a variety of solid or liquid media types, including but not limited to Helellea agar or tryptic soy agar. The cultures are typically incubated at approximately 25-30° C. for a period of time sufficient to produce maximum levels of cells, generally at least 2448 hours. In the alternative to growth on solid media, it is also envisioned that the strain may be grown in liquid culture. Without being limited thereto, conventional tryptic soy broth is preferred. The production of the vaccine in this manner may be conducted by stationary culture of the strain at 25-30° C. for 5 to 7 days. All-vegetable based fermentation media are also preferred for use herein, as the use thereof eliminates the risks of the presence of animal products and infectious agents in the final vaccine product.

Following completion of the propagation, the resultant culture of *A. hydrophila* strains C1B and K134B may be recovered for use as a vaccine. Cells, particularly those produced by liquid culture, may be optionally concentrated, for example, by centrifugation or filtration. As a practical matter, it is envisioned that commercial formulations of the vaccine, particularly those to be administered by bath immersion, may be prepared directly from the culture, thereby obviating the need for any purification steps.

Live cells of the *A. hydrophila* strain are prepared for administration by formulation in an immunologically effective amount or dosage to the fish. The dose may further include pharmaceutically acceptable carriers and adjuvants known in the art. Although, the vaccine may contain levels as low as about $5 \times 10^6$ cells (CFU) of *A. hydrophila*/mL of bath medium, in the preferred embodiment, the vaccine will contain about $1 \times 10^8$ cells (CFU) of *A. hydrophila*/mL of bath medium. Depending on fish size, for an intraperitoneal (IP) injection routine, a preferred dose in a fish would be about 0.1 mL of $1 \times 10^6$ CFU/fish. Although greater amounts of cells may be administered, use of such higher levels is generally considered impractical.

As noted above, the cells may be formulated in an optional, pharmaceutically acceptable carrier such as water, physiological saline, mineral oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials. The microparticles may be composed of any biocompatible matrix materials as are conventional in the art, including but not limited to, agar and polyacrylate. The practitioner skilled in the art will recognize that other carriers or adjuvants may be used as well. For example, other adjuvants which may be used are described by Webb and Winkelstein (In: *Basic & Clinical Immunology*, 1984. Stites et al. (Eds.), Fifth Edition, Lange Medical Publications, Los Altos, Calif., pages 282-285), the contents of which are incorporated by reference herein.

The vaccines of the invention may be administered to the subject animal by any convenient route which enables the cells to elicit an immune response, such as by IP or intramuscular injection, bath immersion, oral administration, or nasal administration. However, IP injection or bath immersion is preferred for primary immunization, while oral immunization is preferred for secondary or booster immunization, when necessary. It is also envisioned that the surface of the fish may be punctured such as described by Nakanishi et al. (2002. *Vaccine* 20:3764-3769) or otherwise abraded or slightly descaled, prior to or during bath immersion, to facilitate exposure of the vaccine to the animal's immune system.

The vaccine may be administered in a single dose or in a plurality of doses. Dependent upon rearing conditions, the vaccine may be administered in multiple doses, the timing of which may be readily determined by the skilled artisan.

Vaccination against infection by *A. hydrophila* by bath immersion immunization offers several advantages over other routes of immunization. Among these advantages are lower cost per fish immunized, mass immunization of large numbers of fish, reduced stress, significantly higher rates of fish survival and the absence of adverse reactions to vaccination. Furthermore, bath immersion vaccination is an effective method for mass vaccination of smaller fish that cannot be injected or subjected to skin punctures. Alternatively, IP injection of commercially available fish vaccines is commonly employed on fresh or marine aquaculture farms due to their reliability and high efficacy despite high cost per fish immunized and stress to the fish.

EXAMPLES

Having now generally described this invention, the same will be better understood by reference to certain specific examples, which are included herein only to further illustrate the invention and are not intended to limit the scope of the invention as defined by the claims.

Example 1

Process of Developing Resistant Mutants of *Aeromonas hydrophila*

The procedure used to produce the *A. hydrophila* vaccine mutants was modified from that described in Shurig et al., supra, by using a lower initial concentration of rifampicin and ending at 320 µg/ml after 44 passages instead of 51 passages and by omitting the penicillin step.

Tryptic soy agar (TSA) plates for the cultivation of *A. hydrophila* were made according to the procedure of Klesius et al. (1999. *Bulletin European Assoc. Fish Pathologists* 19(4): 156-158). Forty g soybean-casein digest agar was added to one liter of distilled water. The medium was heated until dissolution. The medium was then autoclaved at 121-124° C. for 15 min, poured into sterile petri dishes (15 mL per dish) and allowed to solidify before refrigeration.

Native isolates of *A. hydrophila* were obtained from sick tilapia or previously obtained lyophilized stocks. Isolates of *A. hydrophila* were then identified by standard biochemical tests as set forth in *Bergey's Manual of Determinative Bacteriology* (Holt et al., Eds. 1994. Williams & Wilkins, Baltimore, Md.) prior to use in the development of rifampicin-resistant *A. hydrophila* strains. After identification, the process of forming rifampicin-resistant isolates of *A. hydrophila* was begun. Rifampicin-supplemented modified TSA plates were prepared as follows: Modified TSA was made as described above and sterilized at 121-124° C. for 15 min. After sterilization, the correct amount of rifampicin (3-[4-methylpiperazinyl-iminomethyl]rifamycin SV; Sigma Chemical Co., St. Louis, Mo.) was added to the media prior to its solidification and 15 ml of the resulting mixture was poured into separate petri dishes and allowed to solidify prior to refrigerated storage.

Initial cultures of the native isolates of *A. hydrophila* were grown on modified TSA plates which were incubated at 25±2° C. for 24-48 hr or until 1-2 mm white colonies were observed. A single *A. hydrophila* colony was then picked with a sterile inoculating loop and streaked onto a rifampicin-supplemented, modified TSA plate containing the correct concentration of the antibiotic. For the initial passage, rifampicin was present in the modified TSA at a concentration of 2.5 µg/ml. The rifampicin-supplemented modified TSA which was streaked with the aforementioned native isolate of *A. hydrophila* was then incubated for 2448 hr at 25±2° C. and observed for bacterial growth. Single colonies of *A. hydrophila* which grew on the rifampicin-supplemented medium were then picked and placed onto the next concentration of rifampicin (5 µg/ml) modified TSA plates. If growth occurred, a single colony was harvested and placed on an agar medium containing the next higher concentration of rifampicin (10 µg/ml). If the harvested colony failed to grow, it was repeatedly passed on a medium containing the last concentration of rifampicin at which growth successfully occurred, before being placed on the next higher concentration of rifampicin-containing medium. This process was repeated until a colony capable of growing on a medium containing a rifampicin concentration of 320 µg/ml was created.

Following the protocol described above, five isolates *A. hydrophila* designated K83B, K106K, K134B, Veronii, and C1B were cultured separately on TSA containing rifampicin. The protocol followed to successfully obtain two rifampicin-resistant isolates is shown in the following listing of the concentrations used and the number of passages (P) at each concentration: 2.5 mg/mL (5 P), 5 mg/ml (5 P), 10 mg/ml (5 P), 20 mg/ml (5 P), 40 mg/ml (5 P), 60 mg/ml (3 P), 80 mg/ml (3 P), 100 mg/ml (3 P), 120 mg/ml (3), 140 mg/ml (3 P), 180 mg//ml (3 P), and 320 mg/ml (44 P).

Two of the five *A. hydrophila* isolates were chemically mutated with rifampicin to avirulent forms of their virulent parents. Colonies of the avirulent mutants, K134B and C1B, designated NRRL-B-50040 and NRRL-B-50041, respectively, have been cultured on 320 mg/ml of rifampicin for more than 44 passages. NRRL-B-50040 and NRRL-B-50041 can survive and reproduce on a media containing 320 µg/ml rifampicin without negative effect. Biochemical characteristics of the *A. hydrophila* NRRL-B-50041 and NRRL-B-50040 are identical to *A. hydrophila* as described in Bergey's Manual of Determinative Bacteriology, herein incorporated by reference.

Example 2

Selection of the Avirulent Mutants and Their Safety in Nile Tilapia

For this experiment, tilapia were treated in a 57 L aquarium supplied with flow through water at approximately 30° C. with aeration. Ten tilapia (*O. niloticus*) with an average weight of 15-20 grams were in each treatment group: The parent and rifampicin mutant of five *A. hydrophila* isolates (K83B, K106K, K134B, Veronii, and C1B) and control, i.e., 11 treatment groups. The fish were habituated over a 24 h period and fed to satiation with Aquamax Grower 400.

The number of colony forming units CFU/mL was determined through a dilution series. The parent and rifampicin mutant of five *A. hydrophila* isolates (K83B, K106K, K134B, Veronii, and C1B) were streaked onto sheep blood agar and the plates allowed to incubate for 24 h at 30° C. in an atmosphere of air. A diluting solution of 0.1% peptone water was prepared. After 24 h, the cultures were harvested and the inoculum was matched to McFarland standard 10 (approximately OD 1.4) using a spectrophotometer. The inocula were placed in an ice bath in preparation for injection. Each inoculum was plated at 1:10 dilutions of $10^4$ to $10^7$ on TSA in triplicate using a spiral plater. The plates were incubated at 30° C. for 24 h in air. After 24 h, the colonies were counted using the method of Spiral Biotech and recorded. The average number of CFU/mL was calculated and the CFU to be received by the fish determined.

Ten fish each received 0.1 mL of each isolate at a concentration of $10^8$ CFU/fish via intraperitoneal (IP) injection (Table 1). The fish of each treatment were kept in separate tanks maintained at approximately 30° C. and fed to satiation. The control fish were IP injected with saline only (N=10). Fish were observed daily, post injection, for signs of disease. Vaccinated and control fish were held for 14 days following vaccination before they were challenged with $8 \times 10^6$ CFU/fish virulent *A. hydrophila*.

The results showed that two of the five *Aeromonas hydrophila* isolates (40%) were chemically mutated with rifampicin to avirulent forms of their virulent parents. The avirulent mutants were K134B and C1B.

TABLE 1

Selection and safety of *A. hydrophila* rifampicin (Rif)-mutants in Nile tilapia.

| Date | Isolate # | Treatment[a] | # Dead[b] | % Mortality |
|---|---|---|---|---|
| Oct. 31, 2007 | K83B | mutant | 7 | 70 |
| Oct. 31, 2007 | K83B | parent | 10 | 100 |
| Oct. 31, 2007 | K106K | mutant | 9 | 90 |
| Oct. 31, 2007 | K106K | parent | 9 | 90 |
| Oct. 31, 2007 | K134B | mutant | 0 | 0 |
| Oct. 31, 2007 | K134B | parent | 6 | 60 |
| Oct. 31, 2007 | Veronii | mutant | 2 | 20 |
| Oct. 31, 2007 | Veronii | parent | 4 | 40 |
| Oct. 31, 2007 | C1B | mutant | 0 | 0 |
| Oct. 31, 2007 | C1B | parent | 6 | 60 |
| Oct. 31, 2007 | Control | Saline | 0 | 0 |

[a]Rif-mutant and its parent or wild type; The Rif-mutant and parent was intraperitonally (IP) injected at concentration of $5 \times 10^8$ colony forming units (CFU)/fish.
[b]Cumulative mortality out of 10 fish at 14 days post challenge.

Example 3

Vaccine Trials with *Aeromonas hydrophila* C1B and K134B Mutants in Nile Tilapia Nile tilapia were vaccinated by bath immersion and by IP injection. In the bath immersion vaccination method, the *A. hydrophila* rifampicin (Rif) mutant C1B (NRRL-B-50041 or Rif-mutant K134B (NRRL-B-50040) are added at treatment concentrations of $5 \times 10^5$ CFU/mL and $5 \times 10^6$ CFU/mL to 8 L of water for 10 min at a water temperature of 30° C. Vaccinated and control fish were then held under cohabitation conditions for 14 days following vaccination before they were challenged with virulent *A. hydrophila* at a dosage of $8 \times 10^6$ CFU/fish. Cohabitation, i.e., groups of fish being held in the same rearing unit, is regarded as one of the best models for evaluation of vaccine potency because it most mimics natural conditions of pathogen transfer. Sham-vaccinated (control) and vaccinated cohabitants are differentiated by a non-invasive and non-lethal, marking technique utilizing the fluorescent chromophore calcein (Klesius et al. 2006. *Fish and Shellfish Immunology* 20: 20-28). No fish died after the vaccination. Results of experimental challenge are presented as relative percent survival (RPS) as described by Amend (supra) and described above.

A positive effect by vaccination is a RPS greater than 60%. At 14 days post vaccination (DPV), the relative percent survival (RPS) after immunization with the Rif-C1B mutant was 61.5% and 76.5% at concentrations of $5 \times 10^5$ CFU/mL and $5 \times 10^6$ CFU/mL, respectively (Table 2). In this study, mortality in an equivalent group of 20 untreated controls was 65% and 85% versus 20% and 25% mortality in the 20 vaccinated fish.

Tilapia were vaccinated with *A. hydrophila* Rif-C1B mutant by IP injection. The average weight of the fish was 15-20 grams. Fish were immunized by IP with 0.1 mL of $1 \times 10^6$ CFU/mL of the Rif-C1B mutant in tanks of 10 fish/tank. Ten tilapia were injected mL with TSB to serve as control fish (i.e., non-vaccinated). Vaccinated and control fish were held for 14 days following vaccination before they were challenged with virulent *A. hydrophila*. The results showed that significant survival were provided in the vaccinated fish (Table 2). The RPS in vaccinates (Rif-C1B mutant) administered $1 \times 10^6$ CFU/mL by IP injection was 63.3%. Mortality in an equivalent group of 20 untreated controls was 65% versus 25% mortality in the 20 vaccinated fish.

TABLE 2

Relative percent survival for bath immersion and IP routes of immunization with *A. hydrophila* Rif-C1B Mutant[a]

| Rif-C1B Mutant Immunization | % Cumulative mortality in Control Fish (Tryptic Soy Broth)[b] | % Cumulative mortality in Vaccinated Fish[c] | Relative % Survival RPS |
|---|---|---|---|
| Bath Immersion | | | |
| $5 \times 10^5$ CFU/mL | 65 | 25 | 61.5% |
| $5 \times 10^6$ CFU/mL | 85 | 20 | 76.5% |
| TSB 36 mL/8L | 0 | 0 | |
| IP | | | |
| $5 \times 10^6$ CFU/fish | 65 | 25 | 63.3% |
| 0.1 mL TSB/fish | 0 | 0 | |

[a]20 vaccinates and 20 control by cohabitation
[b]Cumulative mortality at 14 days post challenge with $8 \times 10^6$ colony forming units (CFU)/fish in the control fish.
[c]Cumulative mortality at 14 days post challenge with $8 \times 10^6$ colony forming units (CFU)/fish in the vaccinated fish.

Bath immersion and IP immunizations with the *A. hydrophila* Rif-K134B mutant isolate (Table 3) were carried out in the same manner as described for the Rif-C1B mutant isolate. The relative percent survival (RPS) at 14 DPV after immunization with the Rif-K134B mutant was 36.8% and 33.3% at concentrations of $5 \times 10^5$ CFU/mL and $5 \times 10^6$ CFU/mL, respectively (Table 3). Mortality in an equivalent group of 20 untreated controls was 95% and 65% versus 60% and 40% mortality in the 20 vaccinated fish.

In the group immunized IP with Rif-K134B mutant, the RPS was 25.1%. Mortality in an equivalent group of 20 untreated controls was 65% versus 50% mortality in the 20 vaccinated fish.

TABLE 3

Relative percent survival for bath immersion and IP routes of immunization with *A. hydrophila* Rif-K134B Mutant[a]

| Rif-C134B Mutant Immunization | % Cumulative mortality in Control Fish (Tryptic Soy Broth)[b] | % Cumulative mortality in Vaccinated Fish[c] | Relative % Survival RPS |
|---|---|---|---|
| Bath Immersion | | | |
| $5 \times 10^5$ CFU/mL | 95 | 60 | 36.8% |
| $5 \times 10^6$ CFU/mL | 60 | 40 | 33.3% |
| TSB 36 mL/8L | 0 | 0 | |

TABLE 3-continued

Relative percent survival for bath immersion and IP routes of immunization with *A. hydrophila* Rif-K134B Mutant[a]

| Rif-C134B Mutant Immunization | % Cumulative mortality in Control Fish (Tryptic Soy Broth)[b] | % Cumulative mortality in Vaccinated Fish[c] | Relative % Survival RPS |
|---|---|---|---|
| IP | | | |
| 5 × 10⁶ CFU/fish | 65 | 50 | 25.1% |
| 0.1 mL TSB/fish | 0 | 0 | |

[a]20 vaccinates and 20 control by cohabitation.
[b]Cumulative % mortality at 14 days post challenge with 8 × 10⁶ (CFU)/fish in the control fish.
[c]Cumulative % mortality at 14 days post challenge with 8 × 10⁶ (CFU)/fish in the vaccinated fish.

Thus, the vaccine trials showed that the Rif-C1B mutant gave a higher RPS than *A. hydrophila* Rif-K134B mutant by both bath immersion and IP injection routes of immunization in Nile tilapia.

Example 4

Vaccine Trials with *Aeromonas hydrophila* in Channel Catfish Fry

Channel catfish fry were vaccinated by bath immersion. The *A. hydrophila* Rif mutant C1B (NRRL-B-50041 or Rif-mutant K134B (NRRL-B-50040) are added at treatment concentrations of 5×10⁶ CFU/mL and 1×10⁸ CFU/mL to 8 L water for 10 min at a water temperature of 30° C. Vaccinated and control fish were then held under cohabitation conditions for 21 days following vaccination before they were challenged with virulent *A. hydrophila* at a dosage of 8×10⁶ CFU/fish. No fish died after the vaccination. Results of experimental challenge are presented as relative percent survival (RPS) as described by Amend (supra) and described above.

At 14 days post vaccination (DPV), the relative percent survival (RPS) after immunization with both the *A. hydrophila* Rif-C1B mutant and the Rif-K134B was 50% at a concentration of 5×10⁶ CFU/mL and 100% when immunized with 1×10⁸CFU/mL (Table 4). In this study, mortality in an equivalent group of 20 untreated controls was 50% and 0-30% versus 25% and 0% mortality in the 20 vaccinated fish.

TABLE 4

Relative percent survival for bath immersion immunization with *A. hydrophila* Rif-C1B Mutant.[a]

| Rif-C1B Mutant Immunization Bath Immersion | % Cumulative mortality in Control Fish (Tryptic Soy Broth)[b] | % Cumulative mortality in Vaccinated Fish[c] | Relative % Survival RPS |
|---|---|---|---|
| 5 × 10⁶ CFU/mL Rif-C1B | 50 | 25 | 50% |
| 1 × 10⁸ CFU/mL Rif-C1B | 30 | 0 | 100% |
| TSB 36 mL/8L | 0 | 0 | |
| 5 × 10⁶ CFU/mL Rif-K134B | 50 | 25 | 50% |
| 1 × 10⁸ CFU/mL Rif-K134B | 20 | 0 | 100% |
| TSB 36 mL/8L | 0 | 0 | |

[a]20 vaccinates and 20 control by cohabitation
[b]Cumulative % mortality at 14 days post challenge with 8 × 10⁶ colony forming units (CFU)/fish in the control fish.
[c]Cumulative % mortality at 14 days post challenge with 8 × 10⁶ colony forming units (CFU)/fish in the vaccinated fish.

Thus, the vaccine trials showed that in channel catfish, bath immunization with *A. hydrophila* Rif-C1B and Rif-K134B mutants at a concentration of 1×10⁸CFU/mL produced a high RPS, 100%.

Example 5

LPS Profiles of Virulent *A. hydrophila* Isolates and Avirulent Rif-Resistant Mutants Four *A. hydrophila* cultures comprising the virulent parents C1B and K134B and the avirluent Rif-mutants C1B and K124B were grown in 5 ml of TSB for 24 hours at 28° C. The cultures were centrifuged at 3000 g for 15 minutes. LPS was extracted from the pelleted cells using LPS extraction kit #17141 according the manufacture instructions (iNtRON, Biotechology, Korea). The LPS extracts were diluted in electrophoresis sample buffer. The LPS extracts were electrophoresis using discontinous sodium dodesyl sulfate polyacrylamide gel electrophoresis (SDS-PAGE) on a 4% stacking gel and 20% spacing gel (Laemmli U.K. 1970. *Nature* 227:68-685). The SDS-PAGE was run at 25 mAmp for 90 minutes. The SDS-PAGE gel was silver stained according to the manufactures instructions (BioRad, Hercules, Calif.).

The LPS profiles of the *A. hydrophila* Rif-mutants C1B (NRRL-50041) and K134B (NRRL-50040) were compared with those of their wild-type virulent parents, the C1B parent strain and the K134B parent strain, using SDS-PAGE followed by silver staining. The characteristics ladder-like banding pattern of LPS from Gram-negative bacteria was not observed in the Rif-resistant avirulent mutants C1B (Lane 3) and K134B (Lane 5) as compared to the virulent parent strains C1B (Lane 2) and K134B (Lane 4). Most of the LPS bands ranging from about 25 to 40 kDa were absent from the C1B (Lane 3) and K134B (Lane 5) Rif-resistant avirulent mutants, indicating that the LPS produced by the mutants were significantly different (FIG. 1). The virulent parents C1B (Lane 2) and K134B (Lane 4) shared similar LPS banding patterns, although the K134B bands were smaller.

Two rifampicin-resistant attenuated *A. hydrophila* isolates, were deposited on May 4, 2007, in the Agricultural Research Service Culture Collection in Peoria, Ill., and have been assigned Deposit Numbers NRRL B-50040 and NRRL B-50041 as a patent deposit under the Budapest Treaty on the International Recognition of the Deposit of Microorganisms for the Purposes of Patent Procedure. The subject isolates have been deposited under conditions that assure that access to the isolates will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject isolate deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the isolates. The depositor acknowledges the duty to replace the deposits should the depository be unable to furnish a sample when requested, due to the condition of the deposits. All restrictions on the availability to the public of the subject isolate deposits will be irrevocably removed upon the granting of a patent disclosing it.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated attenuated strain of *Aeromonas hydrophila* resistant to rifampicin and effective for eliciting an immune response in fish which is protective against infection by the virulent *Aeromonas hydrophila* parent strain K134B wherein said isolated attenuated strain of *Aeromonas hydrophila* is rifampicin (Rif) mutant K134B mutant deposited at the Agricultural Research Service Culture Collection under Accession Number NRRL-B-50040.

2. An isolated attenuated strain of *Aeromonas hydrophila* resistant to rifampicin and effective for eliciting an immune response in fish which is protective against infection by the virulent *Aeromonas hydrophila* parent strain C1B wherein said isolated attenuated strain of *Aeromonas hydrophila* is Rif-mutant C1B mutant deposited at the Agricultural Research Service Culture Collection under Accession Number NRRL-B-50041.

3. A vaccine composition for protecting fish against infection by the virulent *Aeromonas hydrophila* parent strain K134B comprising: (1) an immunologically effective amount of an isolated attenuated rifampicin-resistant mutant *A. hydrophila* strain; and (2) a carrier, wherein the isolated attenuated mutant strain is Rif-mutant K134B mutant deposited at the Agricultural Research Service Culture Collection under Accession Number NRRL-B-50041.

4. The vaccine composition of claim 3, wherein said carrier is water.

5. A vaccine composition for protecting fish against infection by the virulent *Aeromonas hydrophila* parent strain C1B comprising: (1) an immunologically effective amount of an isolated attenuated rifampicin-resistant mutant *A. hydrophila* strain; and (2) a carrier, wherein the isolated attenuated mutant strain is Rif-mutant C1B mutant deposited at the Agricultural Research Service Culture Collection under Accession Number NRRL-B-50041.

6. The vaccine composition of claim 5, wherein said carrier is water.

7. A method of providing protection for fish against infection by the virulent *Aeromonas hydrophila* parent strain C1B comprising administering to said fish the composition of claim 5.

8. The method of claim 7, wherein said fish is selected from the group consisting of tilapia and channel catfish.

9. The method of claim 7, wherein said administering is by intraperitoneal injection or immersion of said fish in an aqueous medium containing said vaccine.

10. The method of claim 7, wherein said immunologically effective amount of said isolated attenuated mutant *A. hydrophila* strain is present in the aqueous medium at a concentration of about $1\times10^5$ CFU/ml to $1\times10^8$ CFU/ml.

11. The method of claim 7, wherein said immunologically effective amount of said isolated attenuated mutant *A. hydrophila* strain for intraperitoneal injection is about $1\times10^6$ CFU/ml/fish.

12. A method of providing protection for fish against infection by the virulent *Aeromonas hydrophila* parent strain K134B comprising administering to said fish the composition of claim 3.

13. The method of claim 12, wherein said fish is selected from the group consisting of tilapia and channel catfish.

14. The method of claim 12, wherein said administering is by intraperitoneal injection or immersion of said fish in an aqueous medium containing said vaccine.

15. The method of claim 12, wherein said immunologically effective amount of said isolated attenuated mutant *A. hydrophila* strain is present in the aqueous medium at a concentration of about $1\times10^5$ CFU/ml to $1\times10^8$ CFU/ml.

16. The method of claim 12, wherein said immunologically effective amount of said isolated attenuated mutant *A. hydrophila* strain for intraperitoneal injection is about $1\times10^6$ CFU/ml/fish.

* * * * *